(12) United States Patent
Kempanna et al.

(10) Patent No.: US 10,896,763 B2
(45) Date of Patent: Jan. 19, 2021

(54) SYSTEM AND METHOD FOR PROVIDING MODEL-BASED TREATMENT RECOMMENDATION VIA INDIVIDUAL-SPECIFIC MACHINE LEARNING MODELS

(71) Applicant: KONINKLIJKE PHILIPS N.V., Eindhoven (NL)

(72) Inventors: Vinutha Kempanna, Bengaluru (IN); Srinivas Hariharan, Bangalore (IN); Siripurapu Mahesh Reddy, Bangalore (IN); Kiran Kumar Yadalam, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 101 days.

(21) Appl. No.: 16/242,350

(22) Filed: Jan. 8, 2019

(65) Prior Publication Data
US 2019/0221317 A1    Jul. 18, 2019

Related U.S. Application Data

(60) Provisional application No. 62/616,474, filed on Jan. 12, 2018.

(51) Int. Cl.
*G16H 50/70* (2018.01)
*G10L 25/54* (2013.01)
(Continued)

(52) U.S. Cl.
CPC .............. *G16H 50/70* (2018.01); *G06N 20/00* (2019.01); *G10L 25/54* (2013.01); *G10L 25/66* (2013.01); *G16H 20/00* (2018.01); *G16H 50/20* (2018.01)

(58) Field of Classification Search
CPC ........ G16H 50/20; G16H 50/70; G16H 20/00; G16H 10/60; G10L 25/66; G10L 25/54;
(Continued)

(56) References Cited

U.S. PATENT DOCUMENTS 7,962,342 B1 * 6/2011 Coughlan ............... G10L 15/22
                                                704/270.1
2006/0136225 A1    6/2006 Kuo et al.
2016/0364536 A1   12/2016 Dascena

FOREIGN PATENT DOCUMENTS

JP    2015068897 A  *  4/2015
WO    1994010666 A1    5/1994
(Continued)

OTHER PUBLICATIONS

Sellam, V. et al., "Classification of Normal and Pathological Voice Using SVM and RBFNN", Journal of Signal and Information Processing, 2014, 5, 1-7.

*Primary Examiner* — Yogeshkumar Patel

(57) ABSTRACT

The present disclosure pertains to a system for providing model-based treatment recommendation via individual-specific machine learning models. In some embodiments, the system (i) obtains an audio recording of an individual, (ii) determines, from the audio recording, one or more utterance-related features of the individual; (iii) performs one or more queries based on the one or more utterance-related features to obtain health information (e.g., utterance-related conditions and treatments provided for the utterance-related conditions) associated with similar individuals having similar utterance-related conditions as the subject; (iv) provides the health information associated with the similar individuals to a machine learning model to train the machine learning model; and (v) provides, subsequent to the training of the machine learning model, the one or more utterance-related (Continued)

features to the machine learning model to determine one or more treatments for the individual.

15 Claims, 4 Drawing Sheets

(51) Int. Cl.
*G10L 25/66* (2013.01)
*G06N 20/00* (2019.01)
*G16H 20/00* (2018.01)
*G16H 50/20* (2018.01)

(58) Field of Classification Search
CPC ...... G10L 25/51; G06N 20/00; G06N 3/0454; G06N 3/084; G06N 7/005
See application file for complete search history.

(56) References Cited

FOREIGN PATENT DOCUMENTS

| WO | 2002059856 A2 | 8/2002 | |
|---|---|---|---|
| WO | WO2002059856 A2 * | 8/2002 | ............. G09B 19/04 |
| WO | WO-2006109268 A1 * | 10/2006 | ............. G10L 15/10 |

* cited by examiner

400

```
┌─────────────────────────────────────────────────────────────┐
│ Extraxt, from the audio recording a set of utterance-related│
│            features of the individual                       │
│                        402                                  │
└─────────────────────────────────────────────────────────────┘

┌─────────────────────────────────────────────────────────────┐
│   Perform a first pattern recognition on the set of         │
│   utterance-related features based on a first pattern       │
│   recognition scheme to determine which of features of      │
│   the set of utterance-related features have abnormalities  │
│                        404                                  │
└─────────────────────────────────────────────────────────────┘

┌─────────────────────────────────────────────────────────────┐
│   Perform a second pattern recognition on the set of        │
│   utterance-related features based on a second pattern      │
│   recognition scheme to determine which of features of      │
│   the set of utterance-related features have abnormalities  │
│                        406                                  │
└─────────────────────────────────────────────────────────────┘

┌─────────────────────────────────────────────────────────────┐
│   Perform the one or more queries (i) based on the one or   │
│   more utterance-related features and (ii) without reliance │
│   on one or more other utterance-related features of the    │
│   set of utterance-related features to obtain the health    │
│   information associated with the similar individuals       │
│                        408                                  │
└─────────────────────────────────────────────────────────────┘

┌─────────────────────────────────────────────────────────────┐
│      Perform one or more queries to obtain health information│
│                        410                                  │
└─────────────────────────────────────────────────────────────┘

┌─────────────────────────────────────────────────────────────┐
│  Provide the health information associated with the similar │
│  individuals to a predictive learning model to train the    │
│  predictive learning model and providing the other health   │
│  information associated with the other similar individuals  │
│  to a second predictive learning model to train the second  │
│  predictive learning model                                  │
│                        412                                  │
└─────────────────────────────────────────────────────────────┘

┌─────────────────────────────────────────────────────────────┐
│  Provide the first and second subset of utterance-related   │
│  features to the first and second predictive learning       │
│  models, respectively, to determine one or more treatments  │
│  and one or more other treatments for the individual        │
│                        414                                  │
└─────────────────────────────────────────────────────────────┘

┌─────────────────────────────────────────────────────────────┐
│  Select a set of treatments for the individual from the     │
│  one or more treatments and the one or more other treatment │
│                        416                                  │
└─────────────────────────────────────────────────────────────┘
```

FIG. 4

SYSTEM AND METHOD FOR PROVIDING MODEL-BASED TREATMENT RECOMMENDATION VIA INDIVIDUAL-SPECIFIC MACHINE LEARNING MODELS

CROSS-REFERENCE TO PRIOR APPLICATIONS

This application claims the benefit of U.S. Provisional Application No. 62/616,474, filed on 12 Jan. 2018. This application is hereby incorporated by reference herein.

BACKGROUND

1. Field

The present disclosure pertains to a system and method for providing model-based treatment recommendation.

2. Description of the Related Art

Pediatric patients affected by speech and language disorders may benefit from speech pathology treatment; however, diagnosing speech abnormalities in children particularly can be especially challenging, as children are often scared to speak in a clinical setting. Such patients may feel more comfortable speaking at a remote environment (e.g., at home). Although computer model-assisted remote diagnosis and therapy systems exist, such systems often are not able to accurately diagnose speech pathology issues in a repeatable and consistent manner. For example, while prior art systems may employ prediction models to provide therapy recommendations, such prediction models typically are not tailored for an individual having particular physiological characteristics and experiencing specific speech pathology characteristics.

SUMMARY

Accordingly, system for providing model-based treatment recommendation via individual-specific machine learning models. The system comprises one or more processors or other components. The one or more processors are configured by machine-readable instructions to: obtain an audio recording of an individual; determine, from the audio recording, one or more utterance-related features of the individual, the one or more utterance-related features corresponding to characteristics of the individual's utterances in the audio recording; perform one or more queries based on the one or more utterance-related features to obtain health information associated with similar individuals having similar utterance-related conditions as the subject, the health information indicating utterance-related conditions of the similar individuals and treatments provided to the similar individuals respectively for the utterance-related conditions; provide the health information associated with the similar individuals to a machine learning model to train the machine learning model; and provide, subsequent to the training of the machine learning model, the one or more utterance-related features to the machine learning model to determine one or more treatments for the individual.

Yet another aspect of the present disclosure relates to a method for providing model-based treatment recommendation via individual-specific machine learning models. The method is implemented by one or more processors configured by machine readable instructions. The method comprises: obtaining an audio recording of an individual; determining, from the audio recording, one or more utterance-related features of the individual, the one or more utterance-related features corresponding to characteristics of the individual's utterances in the audio recording; performing a query based on the one or more utterance-related features to obtain health information associated with similar individuals having similar utterance-related conditions as the subject, the health information indicating utterance-related conditions of the similar individuals and treatments provided to the similar individuals respectively for the utterance-related conditions; providing the health information associated with the similar individuals to a machine learning model to train the machine learning model; and providing, subsequent to the training of the machine learning model, the one or more utterance-related features to the machine learning model to determine one or more treatments for the individual.

Still another aspect of present disclosure relates to a system for providing model-based treatment recommendation via individual-specific machine learning models. The system comprises: means for obtaining an audio recording of an individual; means for determining, from the audio recording, one or more utterance-related features of the individual, the one or more utterance-related features corresponding to characteristics of the individual's utterances in the audio recording; means for performing one or more queries based on the one or more utterance-related features to obtain health information associated with similar individuals having similar utterance-related conditions as the subject, the health information indicating utterance-related conditions of the similar individuals and treatments provided to the similar individuals respectively for the utterance-related conditions; means for providing the health information associated with the similar individuals to a machine learning model to train the machine learning model; and means for providing, subsequent to the training of the machine learning model, the one or more utterance-related features to the machine learning model to determine one or more treatments for the individual.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

BRIEF DESCRIPTION OF THE DRAWINGS

FIG. 4 illustrates another exemplary method for providing model-based treatment recommendation via individual specific predictive models, in accordance with one or more embodiments.

DETAILED DESCRIPTION OF EXEMPLARY EMBODIMENTS

Figure 1:
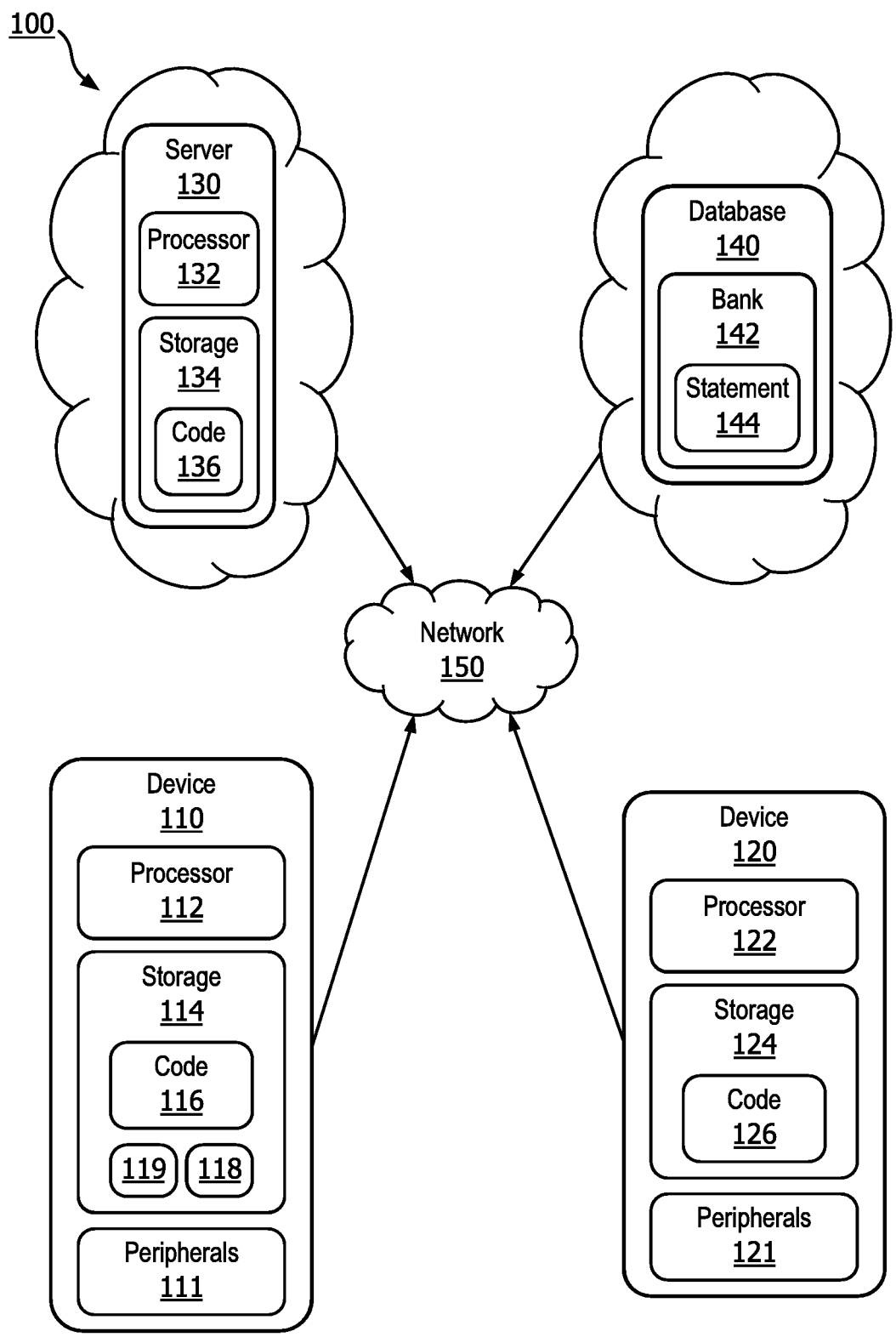
FIGS. 1-2 are schematic illustrations of systems configured to provide model-based treatment recommendation, in accordance with some embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 100 configured to provide model-based treatment recommendation via individual specific predictive models, in accordance with one or more embodiments. System 100 is configured to extract relevant phonetic sounds/acoustic waveforms and classify the extracted information based on one or more patient characteristics. In some embodiments, system 100, via processors 132, is configured to implement pattern recognition and matching to identify abnormalities in one or more of speech waveform, acoustic waveform, speech synthesis, phonetic sound pronunciation waveform, and/or other information. In some embodiments, system 100 is configured to generate a diagnostic report based on the identified abnormalities. In some embodiments, system 100 is configured such that each word, phonetic pronunciation, or other extracted features are queried for pediatric patients with similar conditions (e.g. In some embodiments, system 100 is configured to, via one or more predictive models, provide results of best effective therapies based on matching of similar patients. As such, system 100 includes recording device 110, client device 120, application server 130, database 140, and network 150. As shown in FIG. 1, application server 130 includes processors 132 in communication with storage 134 including application code 136. Processors 132 may be configured to execute application code 136 to carry out the embodiments described herein. Application code 136 may reside on one or more storage devices which may be distributed via application server 130.

As illustrated in FIG. 1, application server 130, with one or more processor 132, is in communication with network 150 via a wired or wireless Internet connection, e.g. Wireless/Ethernet WAN/LAN local network in communication with a hybrid fiber cable (HFC) network. In some embodiments, application server 130 may include an information handling system (IHS) configured as one or more blade server racks implemented as a data center. In some embodiments, application server 130 may be in communication with database 140 for accessing statement banks 142, which include statements 144 and associated classification parameters (not shown). Statements 144 may be utilized for training a prediction model, as discussed in further detail below.

Database 140 may include one or more statement banks 142 storing historical database for problematic words, i.e. statements 144. Statement banks 142 may include statements 144, which are based on a natural language programming approach. Each statement 144 is associated with a particular previous pediatric patient including classification parameters related to the particular pediatric patient. Classification parameters may be based on demographic information of the particular pediatric patient associated with a particular statement of statements 144.

Statements 144 may include demographic information of the previous pediatric patient associated with a particular statement 144. Demographic information of the previous pediatric patient may include, but is not limited to, vital signs information indicating vital signs associated with previous pediatric patients, medical condition information indicating medical conditions experienced by previous pediatric patients including speech abnormalities, treatment information indicating treatments received by previous pediatric patients, outcome information indicating health outcomes for previous pediatric patients, therapies applied to the previous pediatric patient, physical attributes of the previous pediatric patients (e.g. age, weight, height, etc.), geographic location, primary language spoken, accent, and/or other information related to a particular corresponding statement 144.

In some embodiments, statements 144 may include audio waveform, speech waveforms, acoustic waveform, speech synthesis, and/or phonetic sound pronunciation. In some embodiments, database 140 may include sources of training information such as databases, websites, etc., external entities participating with system 100 (e.g., a medical records system of a health care provider that stores medical history information for populations of patients), one or more servers outside of system 100, and/or other sources of information.

In some embodiments, network 150 facilitates communication between recording device 110, and client device 120. Recording device 110 includes peripherals 111, processor 112, storage 114 having code 116, audio 118, and patient characteristics 119 stored thereon. Processor 112 may be configured to execute code 114 for obtaining audio 118 of the pediatric patient and for carrying out embodiments described herein.

In some embodiments, recording device 110 includes peripherals 111, which may include a microphone, speaker, haptic motor, and graphic user interface (not shown). In some embodiments, utilizing a natural language programming approach, recording device 110 may be configured to present the pediatric patient with a multisensory queue that prompts an audio response from the pediatric patient. The audio response is based on a multisensory cue, which may include a pictorial, haptic, or audio representation of a particular word. For example, the graphic user interface of peripherals 111 may present an image of a cat, while the speaker of peripherals 111 may play an audible sound related to the cat, e.g. "meow," which prompts the user to utter a word, e.g. "cat." In some embodiments, the graphic user display of peripherals 111 may present an image of the number 3 and provide a haptic feedback of 3 pulses, which may be implemented by the haptic motor.

In some embodiments, recording device 110 may be configured to, via peripherals 111, record the pediatric patient's utterance responsive to the multisensory queue and store the utterance as audio 118 in storage 114 along with patient characteristics 119. In some embodiments, recording device 110 is configured to input and store patient characteristics 119. Patient characteristics 119 may include demographic information related a pediatric patient (not shown). Demographic information of the pediatric patient may include vital signs information indicating vital signs associated with previous pediatric patients, medical condition information indicating medical conditions experienced by previous pediatric patients, treatment information indicating treatments received by previous pediatric patients, outcome information indicating health outcomes for previous pediatric patients, therapies applied to the previous pediatric patient, physical attributes of the previous pediatric patients (e.g. age, weight, height, etc.), geographic location, primary language spoken, accent, parent heritage/ethnicity, and/or other demographic information.

In some embodiments, recording device 110 includes a smart phone, tablet, laptop, or any other personal computing device. In some embodiments, recording device 110 may be configured to remotely obtain audio 118 of an individual (not shown). In an embodiment, the individual may be a pediatric patient having a speech abnormality. Remotely obtaining audio 118 may include obtaining audio 118 at the pediatric patient's home, or another environment where the pediatric patient is comfortable, other than a physician's office or clinical setting. In some embodiments, recording device 110 is configured to transmit audio 118 of the individual to application server 130, via network 150. As discussed in further detail below, application server 130 may be configured to obtain audio 118 of an individual, and provide model-based treatment recommendations via a diagnostic report, which may be transmitted to client device 120 through network 150.

Figure 2:
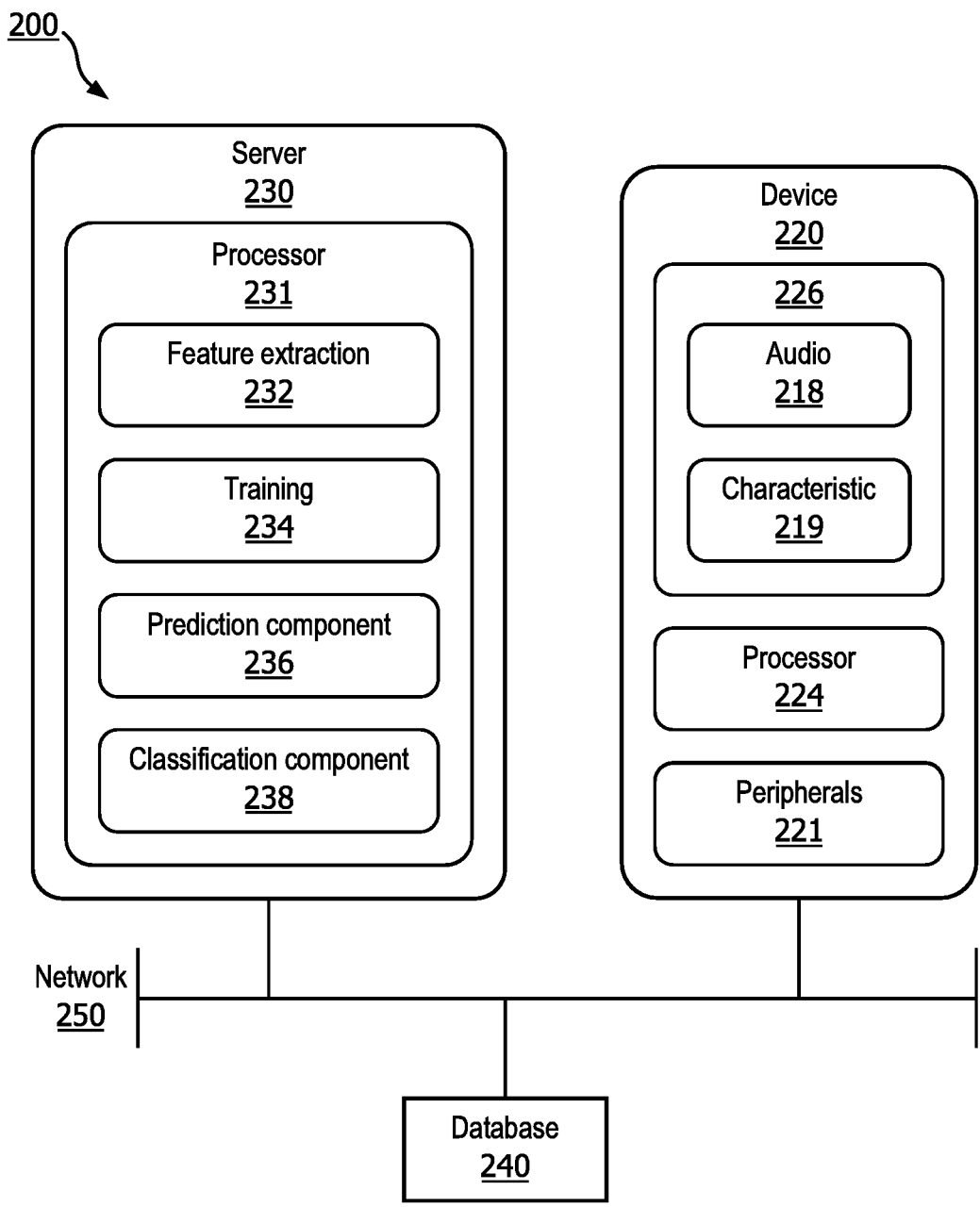

In some embodiments, client device 120 includes processor 122, electronic storage 124 having software code 126 stored thereon and peripherals 121. Processor 122 may be configured to execute software code 126 to carryout out embodiments described herein. Peripherals 121 may include a graphic user interface. As discussed in further detail below, client device 120 may be configured to receive a diagnostic report from application server 130, via network 150. As further discussed in detail below, client device 120 may be configured to receive input from a physician, via graphic user interface of peripherals 121, and transmit the input to application server 130, via network 150. Physician input may be related to one or more queries for implementing model-based treatment recommendation based on desired matching patient characteristics 119, which is discussed in further detail below As shown in FIG. 2, system 200 includes client device 220, application server 230, and database 240, which are all in communication with network 250. As illustrated in FIG. 2, system 200 does not include a recording device similar to that of recording device 110 of FIG. 1. Rather, in some embodiments, client device 220 is configured to transmit audio 218 of the patient to application server 230, including patient characteristics 219. Client device 220 may further be configured to obtain audio 218 of the patient in any manner suitable including, but not limited to, receiving an audio file indirectly, e.g., by having pediatric patients record audio on a personal computing device (not shown) and store audio 218 on a mobile storage device, such as a flash storage contained on a USB thumb drive (not shown), or send via e-mail. As an example, upon receipt of the USB thumb drive or email having the audio file attached, client device 220 may be configured to upload audio 218 of the pediatric patient to application server 230 for providing model-based treatment recommendations via specific prediction models.

In some embodiments, client device 220 includes processors 224, electronic storage 226, or other components. As described above, in some embodiments, client device 220 may include a laptop, a personal computer, a smartphone, a tablet computer, and/or other computing devices. Examples of graphic user interface devices suitable for inclusion in client device 220 include a touch screen, a keypad, touch sensitive and/or physical buttons, switches, a keyboard, knobs, levers, a display, speakers, a microphone, an indicator light, an audible alarm, a printer, and/or other peripheral devices. The present disclosure also contemplates that client device 220 includes a removable storage interface. In this example, information, e.g. audio 218, may be loaded into client device 220 from removable storage (e.g., a smart card, a flash drive, a removable disk) that enables the physicians and pediatric patients (not shown) and/or other users to customize client device 220 and/or system 100, 200. Other exemplary input devices and techniques adapted for use with client device 220 include, but are not limited to, an RS-232 port, RF link, an IR link, a modem (telephone, cable, etc.), and/or other devices.

In some embodiments, application server 230 includes processor 231, which is configured via machine-readable instructions to execute one or more computer program components. The one or more computer program components may comprise one or more of a feature extraction component 232, training component 234, prediction component 236, classification component 238, or other components. Processor 231 may be configured to execute components 232, 234, 236, or 238 by software; hardware; firmware; some combination of software, hardware, or firmware; or other mechanisms for configuring processing capabilities on processor 231.

It should be appreciated that although components 232, 234, 236, and 238 are illustrated in FIG. 2 as being co-located within a single processing unit, in embodiments in which processor 231 comprises multiple processing units, one or more of components 232, 234, 236, and/or 238 may be located remotely from the other components. The description of the functionality provided by the different components 232, 234, 236, and/or 238 described below is for illustrative purposes, and is not intended to be limiting, as any of components 232, 234, 236, and/or 238 may provide more or less functionality than is described. For example, one or more of components 232, 234, 236, and/or 238 may be eliminated, and some or all of its functionality may be provided by other components 232, 234, 236, and/or 238. As another example, processor 231 may be configured to execute one or more additional components that may perform some or all of the functionality attributed below to one of components 232, 234, 236, and/or 238.

Classification component 238 is configured to obtain an audio recording of an individual. In some embodiments, classification component 238 may be configured to obtain audio 118, 218 of an individual, via network 250. In some embodiments, obtaining audio 118, 218 of an individual includes obtaining patient characteristics 119, 219 of the individual. Patient characteristics 119, 219 of the individual may be input into system 100, 200 via GUI 122, 222 of client device 120, 220. As discussed above patient characteristics 119, 219 may include various physical characteristics, medical history, and demographic information of the patient. In some embodiments, subsequent to obtaining audio 118, 218, classification component 238 may further be configured to classify audio 118, 218 of the patient based on associated patient characteristics 119, 219 input into client device 120, 220. In some embodiments, recording device 110 of system 100 may be configured to receive patient characteristics 119, 219 and relay patient characteristics 119, 219, via network 150, 250 to application server 130, 230. Classification of audio 118, 218 of the individual is based on medical history, demographic information, and physical characteristics of the patient.

In some embodiments, classification component 238 is configured to perform one or more queries based on one or more utterance-related features to obtain health information associated with similar individuals having similar utterance-related conditions as the subject. In some embodiments, utterance-related features may include the patient characteristics 119, 219 of the patient, physician-selected features, or other features. Characteristics of the patient may include pitch, prosodic disturbances (e.g., speech rate, pauses, intonation, etc.), voicing errors (e.g., incorrectly confusing or substituting voiceless and voiced consonants), increase in errors with increased length of utterances, limited number of consonant sounds, or other characteristics. In some embodiments, one or more such characteristics may be defined by a user (e.g., a physician) as characteristics to be provided as parameters for one or more queries (e.g., if such characteristics exist in an individual's utterances, then automatically selected those characteristics as parameters for the queries). In some embodiments, the health information indicates utterance-related conditions of the similar individuals, treatments provided to the similar individuals respectively for the utterance-related conditions, whether such treatments were successful for the similar individuals, or other information. The utterance-related conditions may include utterance-related features, syndromes/disorders or diseases of the similar individuals, or other conditions.

In some embodiments, classification component 238 is configured to perform the one or more queries (i) based on the one or more utterance-related features and (ii) without reliance on one or more other utterance-related features of a set of utterance-related features (e.g., one or more characteristics of the individual's utterances in the audio recording) to obtain the health information associated with the similar individuals. In this manner, the predictive model is able to generate a new set of data for increasing accuracy of the predictive model. In some embodiments, the one or more queries are based on patient characteristics 119, 219 of a pediatric patient. For example, in some embodiments, a physician utilizing system 100, 200, may send one or more queries based on patient characteristics 119, 219, to classification component 238, to retrieve statements 144 having closely matching attributes to the patient characteristics 119, 219 input by the physician. In some embodiments, classification component 238 is configured to, for each utterance-related feature of the one or more utterance-related features, determine a classification based on demographic information associated with the individual. In some embodiments, classification component 238 is configured to perform the one or more queries based on the classifications of the one or more utterance-related features to obtain the health information associated with the similar individuals.

In some embodiments, classification component 238 is configured to perform the one or more queries (i) based on a first subset of utterance-related features to obtain the health information associated with the similar individuals and (ii) based on a second subset of utterance-related features to obtain other health information associated with other similar individuals having similar utterance-related conditions as the subject. In some embodiments, the other health information indicates other utterance-related conditions of the other similar individuals and other treatments provided to the other similar individuals respectively for the other utterance-related conditions.

In some embodiments, classification component 238 is configured to provide the health information associated with the similar individuals to a machine learning model to train the machine learning model. In some embodiments, classification component 238 is configured to provide, subsequent to the training of the machine learning model (described below), the one or more utterance-related features to the machine learning model to determine one or more treatments for the individual.

In some embodiments, a physician using device 120, 220 may input specific demographic, medical, and physical attributes for training the predictive model with closely associated matches to the patient. Classification component 232, via processors 130, 230, may be configured to receive classification parameters along with patient characteristics 119, 219. Classification parameters are utilized to determine a set of statements 144, 244 for utilizing the most closely matching sets of statements 144, 244 for training the predictive model. In some embodiments, a physician using client device 120, 220 may input classification parameters based on patient characteristics 119, 219 including a set of demographic, physical, and medical characteristics. For example, inputting classification parameters may include inputting a set of desired characteristics such as age, accent type, and geographic location, and known speech abnormalities with implemented therapies. The desired characteristics may be utilized to query database 140, 240 to obtain statements 144 associated with subjects that are most closely matching to a current pediatric patient. The classification parameters may include 10 parameters, 20 parameters, 100 parameters, or more or less parameters. In this manner, classification component 238, via processor 130, 230, may communicate with database 140, 240 to query for waveforms of statements 144 associated with subjects whom most closely match the criteria input by the set of desired characteristics. Statements 144 may be based on one or more of speech waveform recognition, the acoustic waveform recognition, the speech synthesis recognition, or the phonetic sound pronunciation waveform recognition.

In some embodiments, the input criteria may be weighted by relevancy or importance. For example, the physician might be more interested with waveforms of statements 144 associated with male children ages 4-5 but may also desire children whom live in the south western United States and having are of a particular heritage, for example Chinese. The one or more queries may be configured to query the database to provide statements 144 of children ages 4-5 some who may live outside of south western United States but also having Chinese descent or may also return statements 144 of patients living outside of the desired geographic region but closely matching in the other criteria. Classification component 230 may be configured to score each pre-defined statement retrieved from database 140, 240 with a match percentage, the match percentage relating to how closely match the particular pre-defined statement is with the patient characteristics 219 of the subject. In an embodiment, classification component 238 may be configured to only return statements 144 having a threshold matching score. For example, at least a 90% match. The scoring algorithm is configured to return a set of patient characteristics 219 that most closely match the desired characteristics. In some embodiments, device 120, 220 may be configured to update the match threshold and the parameters in real time in order to fetch a different set of predefined statement based on fewer or less parameters.

Statements 144 in the databank may include therapies of the patient. Therapies of the patient may include the type of linguistic training utilized to cure a particular speech impediment, the length of time of the therapy, the efficacy of the therapy, medicines that may be implemented in therapy, and alternative therapies that may be applied.

In some embodiments, classification component 238 is configured to provide the other health information associated with the other similar individuals to a second machine learning model to train the second machine learning model. In some embodiments, classification component 238 is configured to provide, subsequent to the training of the second machine learning model, the second subset of utterance-related features to the second machine learning model to determine one or more other treatments for the individual.

Feature extraction component 232 is configured to determine, from the audio recording, one or more utterance-related features of the individual. In some embodiments, the one or more utterance-related features correspond to characteristics of the individual's utterances in the audio recording. In some embodiments, feature extraction component 232 may be configured to determine, from audio 118, 218, one or more utterance-related features of the individual. In some embodiments, the one or more utterance-related features correspond to characteristics of the individual's utterances in audio 118, 218. Characteristics of the individual's utterances may relate to the way a pediatric patient pronounces statements 144. Characteristics of the individual's utterances may be analyzed by utilizing frequency analysis and spectral analysis.

In some embodiments, a series of transformations may be applied to audio 118, 218 in order to extract feature vectors of audio 118, 218. In some embodiments, an audio waveform or speech signal may be represented by a sequence of speech parameter vectors or speech feature vectors. In speech analysis, the speech waveform can be converted in a series of feature vectors which represent a subsequence of the speech waveform. In some embodiments, a series of Discrete Fourier Transform and/or Fast Fourier Transform may be utilized in order to represent the waveform as a function of x, i.e. f(x). Using the DFT and/or FFT, the input vectors are projected onto an ordered set of orthonormal basis vectors, wherein the output of the DFT and/or FFT corresponds to the ordered set of inner products between the input vector and the ordered set of orthonormal basis vectors. In another embodiment, feature extraction is implemented using Hidden Markov Models (HMMs).

Hidden Markov Models (HMMs) facilitate intuitive and efficient methods of for modeling time-varying spectral vector sequences. Feature extraction using HMMs consists of implementing a variety of frequency matching and spectral analysis to extract feature vectors, a brief overview follows.

A unit of sound can be described by the acoustic model as the phone, for example the word "cat" consists of three phones /k/ /ae/ /t/. For example, the English language consist of approximately 40 phones. The focus of HMMs are to generate a set of statistical models representing the various sounds or phones of speech. Because speech waveforms have a temporal structure that can be encoded as a sequence of spectral vectors spanning the audio frequency range, HMMs may provide an efficient framework for providing models to represent such a sequence of spectral vectors. Feature extraction aims to create a compact representation of the speech waveform. The goal of feature extraction is to minimize the loss of information that distinguishes between words and word syllables or phones.

In some embodiments, feature vectors are extracted every 10 ms using an overlapping analysis window of around 25 ms. In some embodiments, the encoding scheme may be based on mel-frequency cepstral coefficients (MFCCs). MFCCs may be created by utilizing a truncated discrete cosine transformation (DCT) to a log spectral estimate computed by smoothing a Fast Forrier Transform (FFT) with 20 frequency bins distributed non-linearly across the speech spectrum. The non-linear frequency scale used is called a mel-scale and it aims to approximate the response of the human ear. Applying the DCT acts to smooth out the spectral estimate and approximately decorrelate the feature elements. Once the DST is implemented, the first elements represents the average of the log-energy of the frequency bins, which may be replaced by the log-energy of the frame, or removed entirely. Utilizing HMMs, each spoken utterance recorded by the patient may be decomposed into a sequence of feature. In some embodiments, further constraints are incorporated into a related encoding wherein further manipulation of the recorded utterance may be required and is generally known in the art, the details of which are omitted in this disclosure in order not to obfuscate embodiments described herein. While HMMs are particularly well suited for feature extraction of speech waveforms, other methods of feature extraction are known in the art and may be utilized without departing from the scope and spirit of the present disclosure.

In some embodiments, feature extraction component 232 is configured to extract, from the audio recording, a set of utterance-related features of the individual. In some embodiments, each utterance-related feature of the set of utterance-related features corresponds to one or more characteristics of the individual's utterances in the audio recording. In some embodiments, the characteristics of the individual's utterances may include pitch, prosodic disturbances (e.g., speech rate, pauses, intonation, etc.), voicing errors (e.g., incorrectly confusing or substituting voiceless and voiced consonants), increase in errors with increased length of utterances, limited number of consonant sounds, or other characteristics. In some embodiments, the set of utterance-related features may be a set of feature vectors extracted from audio 118, 218 using Hidden Markov Models, as discussed above. In some embodiments, the set of utterance-related features may include a set of feature vectors extracted from audio 118, 218 using a method other than HMMs. In some embodiments, feature extraction component 232 is configured to determine the one or more utterance-related features by identifying the one or more utterance-related features as features having one or more abnormalities based on the pattern recognition (described below).

In some embodiments, feature extraction component 232 is configured to extract, from the audio recording, a set of utterance-related features of the individual. In some embodiments, each utterance-related feature of the set of utterance-related features corresponds to one or more characteristics of the individual's utterances in the audio recording. In some embodiments, feature extraction component 232 is configured to determine the one or more utterance-related features by identifying a first subset of utterance-related features of the individual as features having one or more abnormalities based on the first pattern recognition. In some embodiments, the first subset includes one or more utterance-related features and other utterance-related features. In some embodiments, each utterance-related feature of the first subset corresponds to one or more characteristics of the individual's utterances in the audio recording.

Training component 234 is configured to train a prediction model of prediction component 236 (described below). In some embodiments, the prediction model may be and/or include a neutral network or other prediction model (e.g., a machine learning model or other prediction model) that is trained and utilized for generating predictions (described below). As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function which combines the values of all its inputs together. In some embodiments, each connection (or the neutral unit itself) may have a threshold function such that the signal must surpass the threshold before it is allowed to propagate to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free-flowing, with connections interacting in a more chaotic and complex fashion.

By way of a non-limiting example, the prediction model of prediction component 236 may include a convolutional neural network (CDD). In a CDD, providing an input will output a probability that the input is a particular label. As an exemplar, a CDD may take as an input a multidimensional array with weighted values, e.g. a 32×32 matrix with a depth of 3. The input may include extracted feature vectors of audio 118, 218 represented in a matrix utilizing, for example, HMMs, as discussed above. CDDs operate to output an array with probabilities of certain classes. The CDD includes several layers between the input and output. The first layer, i.e. the convolution layer, receives an input, i.e. the receptive field. The input may include a transposed matrix of feature vectors. For example, the input may be a series of feature vectors of audio 118, 218, which are transposed in matrix form using HMMs.

The convolution layer produces an activation map/feature map by applying a filter, sometimes referred to a kernel or neuron, to the receptive field. The activation map may be obtained by convolving the filter around the receptive field. The filter includes a matrix of smaller dimensions than the input, yet large enough to extract features. As the filter slides across the receptive field the filter is said to convolve around the field. Convolving the receptive field includes multiplying the filter weights with the receptive filed utilizing element multiplication and performing summation to produce a single output. This process is repeated for every position in the receptive field. The product of convolving the filter around the receptive field is an activation map, or feature map. In some implementation, more filters may be applied. Utilizing an increased number of filters will preserve spatial dimensions more accurately. Accordingly, the CDD may have more than one convolution layer. In this manner, each filter acts as a feature identifier.

In some embodiments, features may include particular edges and curves or combination of edges and curves. Filters may include an array consisting of weights, which act as feature identifiers. In this manner, when a feature represented in a filter, corresponds to a feature of the receptive field, the convolution process, i.e. element multiplication and summation, will yield high values where the receptive field contains a feature, in comparison to portions of the receptive field that do not include such a feature will not yield high values. The output of the convolution, i.e. the activation map, becomes the input for the next layer.

In some embodiments, the activation map shows areas that are likely to include the filter kernel. Applying more or less filter provides greater depth of the activation map, which provides more data for predictive analysis. In summary, the filter of the first layer convolves around an input and "activates" when the specific information contained in the filter kernel is contained in the input volume or input area being currently assessed.

In some embodiments, additional layers are interspersed through the one or more convolving layers including rectified linear unit layers (ReLU) and pooling layers (pool). The additional layers, ReLU and pooling layers, provide non-linearity and preservation of dimension that helps to improve the robustness of the network. An exemplary process may include: input→convolution→ReLU→pool→convolution layer→ReLU→Pool→Fully connected. The fully connected layer provides an array including a probability of a particular input belonging to particular class, or outcome.

In some embodiments, the ReLU layer is applied after every convolution layer. The rectified linear unit layer introduces non-linearity to the system. For example, where the convolution layer is linear, i.e. utilizing multiplication and summation, the ReLU uses tan h and sigmoid function and applies the function $f(x)=\max(0, x)$ to all values of the input volume, i.e. receptive field. Accordingly, the ReLU layer increases the non-linear properties of the model and overall network without affecting the receptive fields of the convolution layer.

In some embodiments, the pooling layer may follow the ReLU. The pooling layer, also known as down sampling layer, takes a 2×2 filter and movement stride of the same length and applies to the input volume and outputs a max number in every sub region that the filter convolves around.

While the first convolution layer, utilizing filters, detects low level features, e.g. edges and curves, a second convolution layer may detect higher level features, i.e. combination of edges and combination of curves, i.e. sinusoids. As the network proceeds through each layer, each convolution layer of the preceding activation map produces higher and higher level features. In this manner as the process continues deeper in the network filter neurons have increasing receptive fields and are thus able to consider information from a larger set of data. After the series of Convolution, ReLU, and pooling is repeated, the final layer consists of the fully connected layer (FCL).

The FCL takes the input volume, i.e. the result of the convolution, ReLU, and pooling, and outputs an N-dimensional vector where N is the number of classes that the program has to choose from. The output returns a probability that the original input receptive field in part of each class, e.g. [0.2 0 0 0 0 0.1 0 0.7] for N=7. In summary, the FCL takes an input volume (i.e. the result of convolution, ReLU, and pooling), and determines which features must correlate to a particular class. However, in order to provide an accurate prediction, the prediction model must be trained.

In some embodiments, training the prediction model may comprise utilizing samples of known utterances having known labels, e.g. a recorded statement having known speech abnormalities associated with the statement. Utilizing known labels of utterances, filter values, i.e. weights, may be trained through backpropagation. Backpropagation may include a series of forward pass having randomized weights followed by using the known label to define a loss function. The loss function may include mean squared error (MSE) which may minimize the loss in order to make accurate predictions. Then using a backward pass for many iterations, the weighs are adjusted to minimize the loss until the loss is optimally minimized.

In some embodiments, training component 234 is configured to perform pattern recognition on the set of utterance-related features to determine which of features of the set of utterance-related features have abnormalities.

In some embodiments, training component 234 is configured to perform first pattern recognition on the set of utterance-related features based on a first pattern recognition scheme to determine which of features of the set of utterance-related features have abnormalities. In some embodiments, the first pattern recognition scheme is related to at least one of speech waveform recognition, acoustic waveform recognition, speech synthesis recognition, or phonetic sound pronunciation waveform recognition. In some embodiments, training component 234 is configured to perform second pattern recognition on the set of utterance-related features based on a second pattern recognition scheme to determine which of features of the set of utterance-related features have abnormalities. In some embodiments, the second pattern recognition scheme is related to at least a different one of the speech waveform recognition, the acoustic waveform recognition, the speech synthesis recognition, or the phonetic sound pronunciation waveform recognition.

Prediction component 236 is configured to select a set of treatments for the individual from the one or more treatments and the one or more other treatments. In this manner, training the prediction model may be based on a combination of one or more of speech waveform recognition, acoustic waveform recognition, speech synthesis recognition, or phonetic sound pronunciation waveform recognition, which provides increased accuracy in the therapy by generating increasing data sets for predictive modeling. In some embodiments, prediction component 236 may be configured to determine one or more treatments for the individual. In some embodiments, prediction component 236 may be configured to determine one or more treatments for the individual and output the one or more treatments to be displayed on device 120, 220. In some embodiments, outputting the one or more treatments includes outputting a diagnostic report. The diagnostic report may include further information related to the predictive model including alternate therapies, and demographic information utilized for the prediction.

In some embodiments, system 100, 200 may be configured to send a diagnostic report to client device 140, 240. The diagnostic report may include information related to the set of treatments for the individual and other information relating to the predictive model. In some embodiments, the predictive model may utilize the current patient data of the individual for further training as described above.

Figure 3:
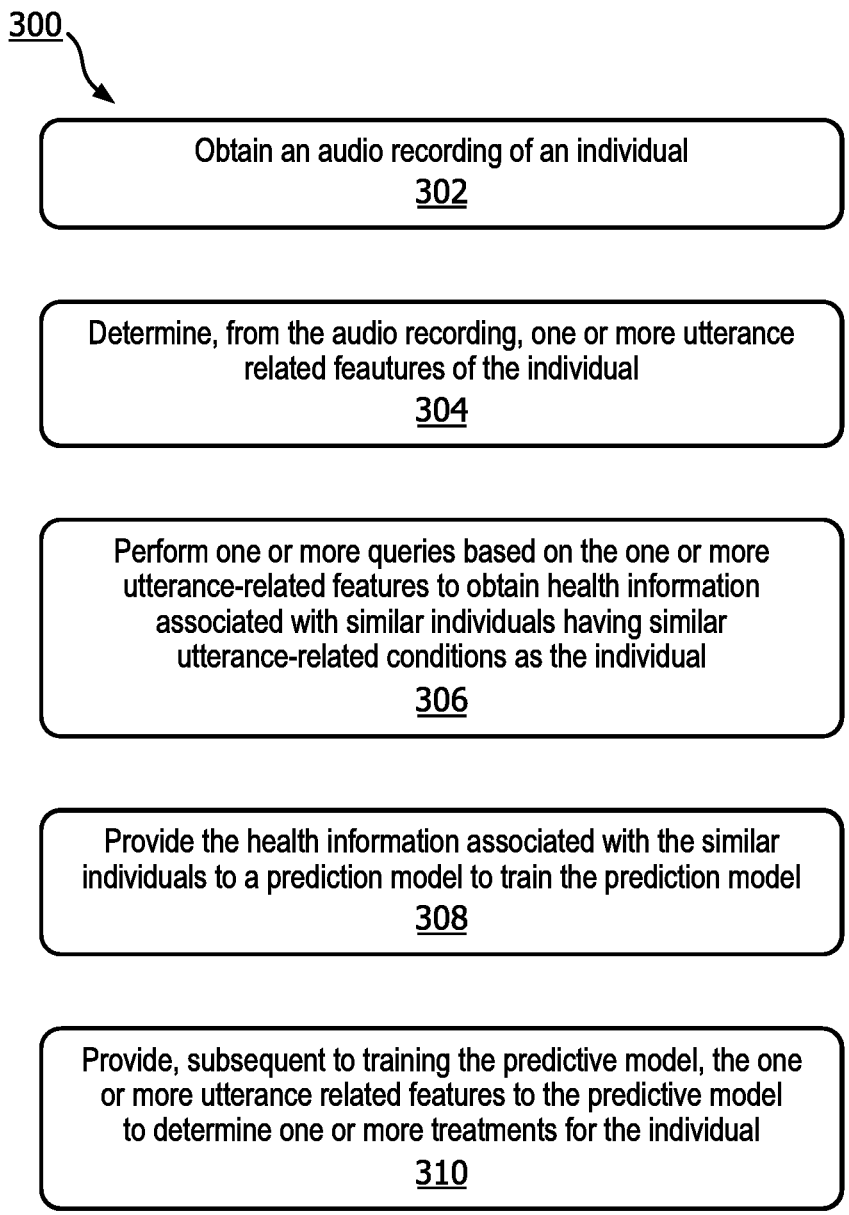
FIG. 3 illustrates a method for providing model-based treatment recommendation via individual specific predictive models, in accordance with one or more embodiments.

FIG. 3 illustrates a method 300 for providing model-based treatment recommendation via individual-specific machine learning models, in accordance with one or more embodiments. Method 300 may be performed with a system. The system comprises one or more processors, or other components. The processors are configured by machine readable instructions to execute computer program components. The computer program components include a feature extraction component, a training component, a prediction component, a classification component, or other components. The operations of method 300 presented below are intended to be illustrative. In some embodiments, method 300 may be accomplished with one or more additional operations not described, or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, a state machine, or other mechanisms for electronically processing information). The devices may include one or more devices executing some or all of the operations of method 300 in response to instructions stored electronically on an electronic storage medium. The processing devices may include one or more devices configured through hardware, firmware, or software to be specifically designed for execution of one or more of the operations of method 300.

At an operation 302, an audio recording of an individual is obtained. In some embodiments, operation 302 is performed by a processor component the same as or similar to classification component 238 (shown in FIG. 2 and described herein).

At an operation 304, one or more utterance-related features of the individual are determined from the audio recording. In some embodiments, the one or more utterance-related features correspond to characteristics of the individual's utterances in the audio recording. In some embodiments, operation 304 is performed by a processor component the same as or similar to feature extraction component 232 (shown in FIG. 2 and described herein).

At an operation 306, a query based on the one or more utterance-related features is performed to obtain health information associated with similar individuals having similar utterance-related conditions as the subject. In some embodiments, the health information indicates utterance-related conditions of the similar individuals and treatments provided to the similar individuals respectively for the utterance-related conditions. In some embodiments, operation 306 is performed by a processor component the same as or similar to classification component 238 (shown in FIG. 2 and described herein).

At an operation 308, the health information associated with the similar individuals is provided to a machine learning model to train the machine learning model. In some embodiments, operation 308 is performed by a processor component the same as or similar to classification component 238 (shown in FIG. 2 and described herein).

At an operation 310, subsequent to the training of the machine learning model (e.g., via training component 234), the one or more utterance-related features are provided to the machine learning model to determine one or more treatments for the individual. In some embodiments, operation 310 is performed by a processor component the same as or similar to prediction component 236 (shown in FIG. 2 and described herein).

FIG. 4 illustrates another exemplary method for providing model-based treatment recommendation via individual specific predictive models, in accordance with one or more embodiments. Method 400 may be performed with a system. The system comprises one or more processors, or other components. The processors are configured by machine readable instructions to execute computer program components. The computer program components include a feature extraction component, a training component, a prediction component, a classification component, or other components. The operations of method 400 presented below are intended to be illustrative. In some embodiments, method 400 may be accomplished with one or more additional operations not described, or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, or other mechanisms for electronically processing information). The devices may include one or more devices executing some or all of the operations of method 400 in response to instructions stored electronically on an electronic storage medium. The processing devices may include one or more devices configured through hardware, firmware, or software to be specifically designed for execution of one or more of the operations of method 400.

At an operation 402, a set of utterance-related features of the individual is extracted from the audio recording. In some embodiments, each utterance-related feature of the set of utterance-related features corresponds to one or more characteristics of the individual's utterances in the audio recording. In some embodiments, operation 402 is performed by a processor component the same as or similar to feature extraction component 232 (shown in FIG. 2 and described herein).

At an operation 404, first pattern recognition is performed on the set of utterance-related features based on a first pattern recognition scheme to determine which of features of the set of utterance-related features have abnormalities. In some embodiments, operation 404 is performed by a processor component the same as or similar to training component 234 (shown in FIG. 2 and described herein).

At an operation 406, second pattern recognition is performed on the set of utterance-related features based on a second pattern recognition scheme to determine which of features of the set of utterance-related features have abnormalities. In some embodiments, operation 406 is performed by a processor component the same as or similar to training component 234 (shown in FIG. 2 and described herein).

At an operation 408, the one or more utterance-related features are determined by identifying a first subset of utterance-related features of the individual as features having one or more abnormalities based on the first pattern recognition. In some embodiments, the first subset comprises one or more utterance-related features and other utterance-related features. In some embodiments each utterance-related feature of the first subset corresponds to one or more characteristics of the individual's utterances in the audio recording. In some embodiments, operation 408 is performed by a processor component the same as or similar to feature extraction component 232 (shown in FIG. 2 and described herein).

At an operation 410, the one or more queries are performed (i) based on the first subset of utterance-related features to obtain the health information associated with the similar individuals and (ii) based on the second subset of utterance-related features to obtain other health information associated with other similar individuals having similar utterance-related conditions as the subject. In some embodiments, the other health information indicates other utterance-related conditions of the other similar individuals and other treatments provided to the other similar individuals respectively for the other utterance-related conditions. In some embodiments, operation 410 is performed by a processor component the same as or similar to classification component 238 (shown in FIG. 2 and described herein).

At an operation 412, the other health information associated with the other similar individuals is provided to a second machine learning model to train the second machine learning model. In some embodiments, operation 412 is performed by a processor component the same as or similar to classification component 238 (shown in FIG. 2 and described herein).

At an operation 414, subsequent to the training of the second machine learning model, the second subset of utterance-related features is provided to the second machine learning model to determine one or more other treatments for the individual. In some embodiments, operation 414 is performed by a processor component the same as or similar to classification component 238 (shown in FIG. 2 and described herein).

At an operation 416, a set of treatments is selected for the individual from the one or more treatments and the one or more other treatments. In some embodiments, operation 416 is performed by a processor component the same as or similar to prediction component 236 (shown in FIG. 2 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system for providing model-based treatment recommendation via individual-specific machine learning models, the system comprising:
    one or more processors configured by machine-readable instructions to:
        obtain an audio recording of an individual;
        determine, from the audio recording, one or more utterance-related features of the individual, the one or more utterance-related features corresponding to characteristics of the individual's utterances in the audio recording;

perform one or more queries based on the one or more utterance-related features to obtain health information associated with similar individuals having similar utterance-related conditions as the subject, the health information indicating utterance-related conditions of the similar individuals and treatments provided to the similar individuals respectively for the utterance-related conditions;

provide the health information associated with the similar individuals to a machine learning model to train the machine learning model; and provide, subsequent to the training of the machine learning model, the one or more utterance-related features to the machine learning model to determine one or more treatments for the individual.

2. The system of claim 1, wherein the one or more processors are further configured to:

extract, from the audio recording, a set of utterance-related features of the individual, each utterance-related feature of the set of utterance-related features corresponding to one or more characteristics of the individual's utterances in the audio recording;

perform pattern recognition on the set of utterance-related features to determine which of features of the set of utterance-related features have abnormalities;

determine the one or more utterance-related features by identifying the one or more utterance-related features as features having one or more abnormalities based on the pattern recognition; and perform the one or more queries (i) based on the one or more utterance-related features and (ii) without reliance on one or more other utterance-related features of the set of utterance-related features to obtain the health information associated with the similar individuals.

3. The system of claim 1, wherein the one or more processors are further configured to:

for each utterance-related feature of the one or more utterance-related features, determine a classification based on demographic information associated with the individual; and perform the one or more queries based on the classifications of the one or more utterance-related features to obtain the health information associated with the similar individuals.

4. The system of claim 1, wherein the one or more processors are further configured to:

extract, from the audio recording, a set of utterance-related features of the individual, each utterance-related feature of the set of utterance-related features corresponding to one or more characteristics of the individual's utterances in the audio recording;

perform first pattern recognition on the set of utterance-related features based on a first pattern recognition scheme to determine which of features of the set of utterance-related features have abnormalities;

perform second pattern recognition on the set of utterance-related features based on a second pattern recognition scheme to determine which of features of the set of utterance-related features have abnormalities;

determine the one or more utterance-related features by identifying a first subset of utterance-related features of the individual as features having one or more abnormalities based on the first pattern recognition, the first subset comprising one or more utterance-related features and other utterance-related features, each utterance-related feature of the first subset corresponding to one or more characteristics of the individual's utterances in the audio recording;

perform the one or more queries (i) based on the first subset of utterance-related features to obtain the health information associated with the similar individuals and (ii) based on the second subset of utterance-related features to obtain other health information associated with other similar individuals having similar utterance-related conditions as the subject, the other health information indicating other utterance-related conditions of the other similar individuals and other treatments provided to the other similar individuals respectively for the other utterance-related conditions;

provide the other health information associated with the other similar individuals to a second machine learning model to train the second machine learning model;

provide, subsequent to the training of the second machine learning model, the second subset of utterance-related features to the second machine learning model to determine one or more other treatments for the individual; and select a set of treatments for the individual from the one or more treatments and the one or more other treatments.

5. The system of claim 4, wherein the first pattern recognition scheme is related to at least one of speech waveform recognition, acoustic waveform recognition, speech synthesis recognition, or phonetic sound pronunciation waveform recognition, and wherein the second pattern recognition scheme is related to at least a different one of the speech waveform recognition, the acoustic waveform recognition, the speech synthesis recognition, or the phonetic sound pronunciation waveform recognition.

6. A method for providing model-based treatment recommendation via individual-specific machine learning models, the method being implemented by one or more processors configured by machine readable instructions, the method comprising:

obtaining an audio recording of an individual;

determining, from the audio recording, one or more utterance-related features of the individual, the one or more utterance-related features corresponding to characteristics of the individual's utterances in the audio recording;

performing a query based on the one or more utterance-related features to obtain health information associated with similar individuals having similar utterance-related conditions as the subject, the health information indicating utterance-related conditions of the similar individuals and treatments provided to the similar individuals respectively for the utterance-related conditions;

providing the health information associated with the similar individuals to a machine learning model to train the machine learning model; and providing, subsequent to the training of the machine learning model, the one or more utterance-related features to the machine learning model to determine one or more treatments for the individual.

7. The method of claim 6, wherein the method further comprises:

extracting, from the audio recording, a set of utterance-related features of the individual, each utterance-related feature of the set of utterance-related features corresponding to one or more characteristics of the individual's utterances in the audio recording;

performing pattern recognition on the set of utterance-related features to determine which of features of the set of utterance-related features have abnormalities;

determining the one or more utterance-related features by identifying the one or more utterance-related features as features having one or more abnormalities based on the pattern recognition; and performing the one or more queries (i) based on the one or more utterance-related features and (ii) without reliance on one or more other utterance-related features of the set of utterance-related features to obtain the health information associated with the similar individuals.

8. The method of claim 6, wherein the method further comprises:

for each utterance-related feature of the one or more utterance-related features, determining a classification based on demographic information associated with the individual; and performing the one or more queries based on the classifications of the one or more utterance-related features to obtain the health information associated with the similar individuals.

9. The method of claim 6, wherein the method further comprises:

extracting, from the audio recording, a set of utterance-related features of the individual, each utterance-related feature of the set of utterance-related features corresponding to one or more characteristics of the individual's utterances in the audio recording;

performing first pattern recognition on the set of utterance-related features based on a first pattern recognition scheme to determine which of features of the set of utterance-related features have abnormalities;

performing second pattern recognition on the set of utterance-related features based on a second pattern recognition scheme to determine which of features of the set of utterance-related features have abnormalities;

determining the one or more utterance-related features by identifying a first subset of utterance-related features of the individual as features having one or more abnormalities based on the first pattern recognition, the first subset comprising one or more utterance-related features and other utterance-related features, each utterance-related feature of the first subset corresponding to one or more characteristics of the individual's utterances in the audio recording;

performing the one or more queries (i) based on the first subset of utterance-related features to obtain the health information associated with the similar individuals and (ii) based on the second subset of utterance-related features to obtain other health information associated with other similar individuals having similar utterance-related conditions as the subject, the other health information indicating other utterance-related conditions of the other similar individuals and other treatments provided to the other similar individuals respectively for the other utterance-related conditions;

providing the other health information associated with the other similar individuals to a second machine learning model to train the second machine learning model;

providing, subsequent to the training of the second machine learning model, the second subset of utterance-related features to the second machine learning model to determine one or more other treatments for the individual; and selecting a set of treatments for the individual from the one or more treatments and the one or more other treatments.

10. The method of claim 9, wherein the first pattern recognition scheme is related to at least one of speech waveform recognition, acoustic waveform recognition, speech synthesis recognition, or phonetic sound pronunciation waveform recognition, and wherein the second pattern recognition scheme is related to at least a different one of the speech waveform recognition, the acoustic waveform recognition, the speech synthesis recognition, or the phonetic sound pronunciation waveform recognition.

11. A system for providing model-based treatment recommendation via individual-specific machine learning models, the system comprising:

means for obtaining an audio recording of an individual;

means for determining, from the audio recording, one or more utterance-related features of the individual, the one or more utterance-related features corresponding to characteristics of the individual's utterances in the audio recording;

means for performing one or more queries based on the one or more utterance-related features to obtain health information associated with similar individuals having similar utterance-related conditions as the subject, the health information indicating utterance-related conditions of the similar individuals and treatments provided to the similar individuals respectively for the utterance-related conditions;

means for providing the health information associated with the similar individuals to a machine learning model to train the machine learning model; and means for providing, subsequent to the training of the machine learning model, the one or more utterance-related features to the machine learning model to determine one or more treatments for the individual.

12. The system of claim 11, wherein the one or more processors are further configured to:

means for extracting, from the audio recording, a set of utterance-related features of the individual, each utterance-related feature of the set of utterance-related features corresponding to one or more characteristics of the individual's utterances in the audio recording;

means for performing pattern recognition on the set of utterance-related features to determine which of features of the set of utterance-related features have abnormalities;

means for determining the one or more utterance-related features by identifying the one or more utterance-related features as features having one or more abnormalities based on the pattern recognition; and means for performing the one or more queries (i) based on the one or more utterance-related features and (ii) without reliance on one or more other utterance-related features of the set of utterance-related features to obtain the health information associated with the similar individuals.

13. The system of claim 11, further comprising:

means for, for each utterance-related feature of the one or more utterance-related features, determining a classification based on demographic information associated with the individual; and means for performing the one or more queries based on the classifications of the one or more utterance-related features to obtain the health information associated with the similar individuals.

14. The system of claim 11, further comprising:

means for extracting, from the audio recording, a set of utterance-related features of the individual, each utterance-related feature of the set of utterance-related features corresponding to one or more characteristics of the individual's utterances in the audio recording;

means for performing first pattern recognition on the set of utterance-related features based on a first pattern recognition scheme to determine which of features of the set of utterance-related features have abnormalities;

means for performing second pattern recognition on the set of utterance-related features based on a second pattern recognition scheme to determine which of features of the set of utterance-related features have abnormalities;

means for determining the one or more utterance-related features by identifying a first subset of utterance-related features of the individual as features having one or more abnormalities based on the first pattern recognition, the first subset comprising one or more utterance-related features and other utterance-related features, each utterance-related feature of the first subset corresponding to one or more characteristics of the individual's utterances in the audio recording;

means for performing the one or more queries (i) based on the first subset of utterance-related features to obtain the health information associated with the similar individuals and (ii) based on the second subset of utterance-related features to obtain other health information associated with other similar individuals having similar utterance-related conditions as the subject, the other health information indicating other utterance-related conditions of the other similar individuals and other treatments provided to the other similar individuals respectively for the other utterance-related conditions;

means for providing the other health information associated with the other similar individuals to a second machine learning model to train the second machine learning model;

means for providing, subsequent to the training of the second machine learning model, the second subset of utterance-related features to the second machine learning model to determine one or more other treatments for the individual; and means for selecting a set of treatments for the individual from the one or more treatments and the one or more other treatments.

15. The system of claim 14, wherein the first pattern recognition scheme is related to at least one of speech waveform recognition, acoustic waveform recognition, speech synthesis recognition, or phonetic sound pronunciation waveform recognition, and wherein the second pattern recognition scheme is related to at least a different one of the speech waveform recognition, the acoustic waveform recognition, the speech synthesis recognition, or the phonetic sound pronunciation waveform recognition.

* * * * *